United States Patent
Nair et al.

(10) Patent No.: US 9,285,358 B2
(45) Date of Patent: Mar. 15, 2016

(54) VITRO METHOD FOR HIGH THROUGHPUT SCREENING OF GENOTOXIC AGENTS IN EUKARYOTIC CELLS

(75) Inventors: Ayyappan Nair, Mawhaw, NJ (US); Madhuri Subbiah, Hyderabad (IN); Gunja Gupta, Jaipur (IN); Lakshmi Rajakrishna, Somasundarapalaya (IN); Pradeep Savanoor, Bangalore (IN); Subbulakshmi Karthikeyan, Bangalore (IN); Salini Krishnan Unni, Bangalore (IN); Ganesh Sambasivam, Bangalore (IN)

(73) Assignee: ANTHEM BIOSCIENCES PVT LTD (IN)

( * ) Notice: Subject to any disclaimer, the term of this patent is extended or adjusted under 35 U.S.C. 154(b) by 37 days.

(21) Appl. No.: 14/110,302

(22) PCT Filed: Apr. 7, 2012

(86) PCT No.: PCT/IB2012/051729
§ 371 (c)(1),
(2), (4) Date: Dec. 27, 2013

(87) PCT Pub. No.: WO2012/137186
PCT Pub. Date: Oct. 11, 2012

(65) Prior Publication Data
US 2014/0148360 A1    May 29, 2014

(30) Foreign Application Priority Data

Apr. 8, 2011   (IN) ............ 1239/CHE/2011

(51) Int. Cl.
*C12N 15/00* (2006.01)
*G01N 33/50* (2006.01)
*C12Q 1/68* (2006.01)

(52) U.S. Cl.
CPC .......... *G01N 33/5014* (2013.01); *C12Q 1/6897* (2013.01); *G01N 33/5023* (2013.01)

(58) Field of Classification Search
None
See application file for complete search history.

(56) References Cited

U.S. PATENT DOCUMENTS 6,344,324 B2    2/2002   Howell et al.

OTHER PUBLICATIONS

Anderson et al., Nature Genetics, 1998, vol. 19, pp. 254-256.*
Aubrecht et al., Future Medicine, 2005, vol. 6, pp. 419-428.*
Anderson et al., Nature, 1998, vol. 19, pp. 254-256.*
International Search Report corresponding to International Application No. PCT/IB2012/051729, dated Jul. 2, 2012; 5 pages.
Zager, V. et al.: 'Development of human cell biosensor system for genotoxicity detection based on DNA damage-induced gene expression', Radiology and Oncology. vol. 44, No. 1, Mar. 2010, ISSN 1318-2099 pp. 42-51.
Potratz, JC. et al.: 'In vivo analyses of UV-irradiation-induced p53 promoter binding using a novel quantitative real-time PCR assay', International Journal of Oncology. vol. 26, No. 2, Feb. 2005, ISSN 1019-6439 pp. 493-498.
Braastad, CD. et al.: 'Constitutive DNase I hypersensitivity of p53-regulated promoters', The Journal of Biological Chemistry vol. 278, No. 10, Mar. 2003, ISSN 002.1-925 pp. 8261-8268.
Eizirik, DL. et al.: 'Genotoxic agents increase expression of growrth arrest and DNA damage—inducible genes gadd 153 and gadd 45 in rat pancreatic islets', Diabetes. vol. 42, No. 5, May 1993, ISSN 0012-1797 pp. 738-745.
Tully, DB. et al.: 'Effects of arsenic, cadmium, chromium, and lead on gene expression regulated by a battery of 13 different promoters in recombinant HepG2 cells', Toxicology and Applied Pharmacology. vol. 168, No. 2, Oct. 2000, ISSN 0041-008X pp. 79-90.
Tchounwou, PB. et al.: 'Differential cytotoxicity and gene expression in human liver carcinoma (Hepg2) cells exposed to arsenic trioxide, and monosodium acid methanearsonate (MSMA)', International Journal of Molecular Sciences. vol. 3, No. 11, Nov. 2002, ISSN 1422-0067 pp. 1117-1132.
Delescluse, C. et al.: 'Induction of cytochrome P450 1 AI gene expression, oxidative stress, and genotoxicity by carbaryl and thiabendazole in transfected human HepG2 and lymphoblastoid cells' Biochemical Pharmacology. vol. 61, No. 4, Feb. 2001, ISSN 0006-2952 pp. 399-407.
Bonderoff, J. et al.: 'Time-dependent increase in ribosome processivity', Nucleic Acids Research. vol. 38, No. 20, Nov. 2010, ISSN 0305-1048 pp. 7054-7067.

* cited by examiner

*Primary Examiner* — Michele K Joike
*Assistant Examiner* — Mindy G Brown
(74) *Attorney, Agent, or Firm* — Carter, DeLuca, Farrell & Schmidt, LLP

(57) ABSTRACT

The present invention relates to a novel method for high throughput detection of wide range of genotoxins in eukaryotic cells wherein the eukaryotic cell based tool combines the ability to detect a broad spectrum of genotoxic signaling events and a simple and reproducible assay technique. The present invention further comprises expression cassettes, vectors, and eukaryotic cell lines for the same.

11 Claims, 6 Drawing Sheets

SEQUENCE LISTING

<160> NUMBER OF SEQ ID NOS: 6

<210> SEQ ID NO 1
<211> LENGTH: 33
<212> TYPE: DNA
<213> ORGANISM: Artificial Sequence
<220> FEATURE:
<223> OTHER INFORMATION: Synthetic

<400> SEQUENCE: 1
gatcgtacat cgatagccac cactgagcct tcc    33

<210> SEQ ID NO 2
<211> LENGTH: 34
<212> TYPE: DNA
<213> ORGANISM: Artificial Sequence
<220> FEATURE:
<223> OTHER INFORMATION: Synthetic

<400> SEQUENCE: 2

```
gtacgatcgc tagcctccgg ctccacaagg aact                                34
```

<210> SEQ ID NO 3
<211> LENGTH: 41
<212> TYPE: DNA
<213> ORGANISM: Artificial Sequence
<220> FEATURE:
<223> OTHER INFORMATION: Synthetic

<400> SEQUENCE: 3

```
gatcgctagc gccgccacca tggccgatgc taagaacatt a                         41
```

<210> SEQ ID NO 4
<211> LENGTH: 30
<212> TYPE: DNA
<213> ORGANISM: Artificial Sequence
<220> FEATURE:
<223> OTHER INFORMATION: Synthetic

<400> SEQUENCE: 4

```
gatcgaattc ttacacggcg atcttgccgc                                      30
```

<210> SEQ ID NO 5
<211> LENGTH: 10510
<212> TYPE: DNA
<213> ORGANISM: Artificial Sequence
<220> FEATURE:
<223> OTHER INFORMATION: Synthetic

<400> SEQUENCE: 5

```
acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata agcttgcct tgagtgcttc aagtagtgtg tgcccgtctg ttgtgtgact    360
ctggtaacta gagatccctc agacccttt agtcagtgtg aaaatctct agcagtggcg    420
cccgaacagg gacctgaaag cgaaagggaa accagagctc tctcgacgca ggactcggct    480
tgctgaagcg cgcacggcaa gaggcgaggg cggcgactg tgagtacgc caaaatttt    540
gactagcgga ggctagaagg agagagatgg gtgcgagagc gtcagtatta agcggggag    600
aattagatcg cgatgggaaa aaattcggtt aaggccaggg ggaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagcaccaa aggaagcttt agacaagata gaggaagagc aaaacaaaag    900
taagaccacc gcacagcaag cggccactga tcttcagacc tggaggagga gatatgaggg    960
acaattggag aagtgaatta tataaatata agtagtaaa aattgaacca ttaggagtag    1020
cacccaccaa ggcaaagaga agagtggtgc agagagaaaa aagagcagtg ggaataggag    1080
ctttgttcct tgggttcttg ggagcagcag gaagcactat gggcgcagcc tcaatgacgc    1140
tgacggtaca ggccagacaa ttattgtctg gtatagtgca gcagcagaac aatttgctga    1200
gggctattga ggcgcaacag catctgttgc aactcacagt ctggggcatc aagcagctcc    1260
```

```
aggcaagaat cctggctgtg aaagatacc taaaggatca acagctcctg gggatttggg      1320
gttgctctgg aaaactcatt tgcaccactg ctgtgccttg aatgctagt tggagtaata      1380 aatctctgga acagattgga atcacacgac ctggatggag tgggacagag aaattaacaa      1440
ttacacaagc ttaatacact ccttaattga agaatcgcaa aaccagcaag aaagaatga      1500 acaagaatta ttggaattag ataaatgggc aagtttgtgg aattggttta acataacaaa      1560
ttggctgtgg tatataaaat tattcataat gatagtagga ggcttggtag gtttaagaat      1620 agttttgct gtactttcta tagtgaatag agttaggcag ggatattcac cattatcgtt      1680
tcagacccac ctcccaaccc cgaggggacc cgacaggccc gaaggaatag aagaagaagg      1740
tggagagaga gacagagaca gatccattcg attagtgaac ggatctcgac ggttaacttt      1800
taaaagaaaa ggggggattg gggggtacag tgcaggggaa agaatagtag acataatagc      1860
aacagacata caaactaaag aattacaaaa acaaattaca aaaattcaaa attttatcga      1920
tagccaccac tgagccttcc tcacatcctc cttcttcagg cttgggcttt ccacctttca      1980
ccattcccct accccatgct gctccaccgc actctgggga ggggctgga ctgggcactc      2040 ttgtccccca ggctgagcct ccctccatcc ctatgctgcc tgcttcccag aacatgctt      2100 gggcagcagg ctgtggctct gattggcttt ctggccatca ggaacatgtc caacatgtt      2160 gagctctggc atagaagagg ctggtggcta ttttgtcctt gggctgcctg ttttcaggga      2220 ggaagggat ggtaggagac aggagacctc taaagacccc aggtaaacct tagcctctta      2280
ctctgaacag ggtatgtgat ctgccagcag gatccttgcg acagggctgg gatctgatgc      2340
atgtgtgctt gtgtgagtgt gtgctgggag tcagattctg tgtgtgactt ttaacagcct      2400
gctcccttgc cttcttcagg gcagaagtcc tcccttagag tgtgtctggg tacacattca      2460
agtgcatggt tgcaaacttt ttttttaaa gcactgaata gtactagaca cttagtaggt      2520
acttaagaaa tattgaatgt cgtggtggtg gtgagctaga agttataaaa aaaattcttt      2580
cccaaaaaca acaacaaaaa gaattatttc attgtgaagc tcagtaccac aaaaattcat      2640
tacaataatt cattacaagc ctttattaaa aaaaattttc tccccaaagt aaacagacag      2700
acaatgtcta gtctatttga aatgcctgaa agcagagggg cttcaaggca gtgggagaag      2760
gtgcctgtcc tctgctggac atttgacaac cagcccttg gatggtttgt atgtatagga      2820
gcgaaggtgc agacagcagt gggggcttaga gtggggtcct gaggctgtgc tgtgggccctt      2880 ctggggttta gccacaatcc tggcctgact ccagggcgag gcaggccaag ggggtctgct      2940
gctgtgtcct cccaccccta cctgggctcc catccccaca gcagaggaga aagaagcctg      3000
tcctccccga ggtcagctgc gttagaggaa gaagactggg catgtctggg cagagatttc      3060
cagactctga gcagcctgag atgtcagtaa ttgtagctgc tccaagcctg ggttctgttt      3120
ttcagtggga tttctgttca gatgaacaat ccatcctctg caattttta aaagcaaaac      3180 tgcaaatgtt tcaggcacag aaaggaggca aaggtgaagt ccaggggagg tcagggtgt      3240 gaggtagatg ggagcggata gacacatcac tcatttctgt gtctgtcaga agaaccagta      3300
gacacttcca gaattgtcct ttatttatgt catctcccata aaccatctgc aaatgagggt      3360
tatttggcat ttttgtcatt ttggaaccac agaaataaag gatgacaagc agagagcccc      3420
gggcaggagg caaaagtcct gtgttccaac tatagtcatt tctttgctgc atgatctgag      3480
ttaggtcacc agacttctct gagccccagt ttccccagca gtgtatacgg gctatgtggg      3540
gagtattcag gagacagaca actcactcgt caaatcctcc ccttcctggc caacaaagct      3600
gctgcaacca caggggtttc ttctgttcag gtgagtgtag ggtgtaggga gattggttca      3660
```

```
atgtccaatt cttctgtttc cctggagatc aggttgccct ttttggtag tctctccaat    3720 tccctccttc ccggaagcat gtgacaatca acaactttgt atacttaagt tcagtggacc    3780
tcaatttcct catctgtgaa ataaacggga ctgaaaaatc attctggcct caagatgctt    3840
tgttggggtg tctaggtgct ccaggtgctt ctgggagagg tgacctagtg agggatcagt    3900
gggaatagag gtgatattgt ggggcttttc tggaaattgc agagaggtgc atcgtttta    3960 taatttatga atttttatgt attaatgtca tcctcctgat cttttcagct gcattgggta    4020
aatccttgcc tgccagagtg ggtcagcggt gagccagaaa gggggctcat tctaacagtg    4080
ctgtgtcctc ctggagagtg ccaactcatt ctccaagtaa aaaaagccag atttgtggct    4140
cacttcgtgg ggaaatgtgt ccagcgcacc aacgcaggcg agggactggg ggaggaggga    4200
agtgccctcc tgcagcacgc gaggttccgg gaccggctgg cctgctggaa ctcggccagg    4260
ctcagctgct ccgcgctggg cagccaggag cctgggcccc ggggagggcg gtcccgggcg    4320
gcgcggtggg ccgagcgcgg gtcgcctcct tgaggcgggc ccgggcgggg cggttgtata    4380
tcagggccgc gctgagctgc gccagctgag gtgtgagcag ctgccgaagt cagttccttg    4440
tggagccgga gctagccacc atggcttcca aggtgtacga ccccgagcaa cgcaaacgca    4500
tgatcactgg gcctcagtgg tgggctcgct gcaagcaaat gaacgtgctg gactccttca    4560
tcaactacta tgattccgag aagcacgccg agaacgccgt gattttctg catggtaacg    4620 ctgcctccag ctacctgtgg aggcacgtcg tgcctcacat cgagcccgtg gctagatgca    4680
tcatccctga tctgatcgga atgggtaagt ccggcaagag cgggaatggc tcatatcgcc    4740
tcctggatca ctacaagtac ctcaccgctt ggttcgagct gctgaacctt ccaaagaaaa    4800
tcatctttgt gggccacgac tgggggggctt gtctggcctt tcactactcc tacgagcacc    4860
aagacaagat caaggccatc gtccatgctg agagtgtcgt ggacgtgatc gagtcctggg    4920
acgagtggcc tgacatcgag gaggatatcg ccctgatcaa gagcgaagag ggcgagaaaa    4980
tggtgcttga gaataacttc ttcgtcgaga ccatgctccc aagcaagatc atgcggaaac    5040
tggagcctga ggagttcgct gcctacctgg agccattcaa ggagaagggc gaggttagac    5100
ggcctaccct ctcctggcct cgcgagatcc ctctcgttaa gggaggcaag cccgacgtcg    5160
tccagattgt ccgcaactac aacgcctacc ttcgggccag cgacgatctg cctaagatgt    5220
tcatcgagtc cgaccctggg ttcttttcca acgctattgt cgagggagct aagaagttcc    5280
ctaacaccga gttcgtgaag gtgaagggcc tccacttcag ccaggaggac gctccagatg    5340
aaatgggtaa gtacatcaag agcttcgtgg agcgcgtgct gaagaacgag cagtaattct    5400
aggcgatcgc tcgagcccgg gaattcgttt aaacctagag cggccgcaag gatctgcgat    5460
cgctccggtg cccgtcagtg ggcagagcgc acatcgccca cagtcccga gaagttgggg    5520 ggaggggtcg gcaattgaac gggtgcctag agaaggtggc gcggggtaaa ctgggaaagt    5580
gatgtcgtgt actggctccg cctttttccc gagggtgggg gagaaccgta tataagtgca    5640
gtagtcgccg tgaacgttct ttttcgcaac gggtttgccg ccagaacaca gctgaagctt    5700
cgaggggctc gcatctctcc ttcacgcgcc cgccgcccta cctgaggccg ccatccacgc    5760
cggttgagtc gcgttctgcc gcctcccgcc tgtggtgcct cctgaactgc gtccgccgtc    5820
taggtaagtt taaagctcag gtcgagaccg ggcctttgtc cggcgctccc ttggagccta    5880
cctagactca gccggctctc cacgctttgc ctgaccctgc ttgctcaact ctacgtcttt    5940
gtttcgtttt ctgttctgcg ccgttacaga tccaagctgt gaccggcgcc tacgctagat    6000
```

```
gaccgagtac aagcccacgg tgcgcctcgc cacccgcgac gacgtcccca gggccgtacg    6060
cacccctcgcc gccgcgttcg ccgactaccc cgccacgcgc cacaccgtcg atccggaccg   6120
ccacatcgag cgggtcaccg agctgcaaga actcttcctc acgcgcgtcg ggctcgacat    6180
cggcaaggtg tgggtcgcgg acgacggcgc cgcggtggcg gtctggacca cgccggagag    6240
cgtcgaagcg ggggcggtgt cgccgagat cggcccgcgc atggccgagt tgagcggttc     6300
ccggctggcc gcgcagcaac agatggaagg cctcctggcg ccgcaccggc caaggagcc     6360
cgcgtggttc ctggccaccg tcggcgtctc gcccgaccac cagggcaagg gtctgggcag    6420
cgccgtcgtg ctccccggag tggaggcggc cgagcgcgcc ggggtgcccg ccttcctgga    6480
gacctccgcg ccccgcaacc tccccttcta cgagcggctc ggcttcaccg tcaccgccga    6540
cgtcgaggtg cccgaaggac cgcgcacctg gtgcatgacc cgcaagcccg gtgcctgagt    6600
cgacaatcaa cctctggatt acaaaatttg tgaaagattg actggtattc ttaactatgt    6660
tgctcctttt acgctatgtg gatacgctgc tttaatgcct ttgtatcatg ctattgcttc    6720
ccgtatggct ttcattttct cctccttgta taaatcctgg ttgctgtctc tttatgagga    6780
gttgtggccc gttgtcaggc aacgtggcgt ggtgtgcact gtgtttgctg acgcaacccc    6840
cactggttgg ggcattgcca ccacctgtca gctccttttcc gggactttcg ctttccccct   6900
ccctattgcc acggcggaac tcatcgccgc ctgccttgcc cgctgctgga caggggctcg    6960
gctgttgggc actgacaatt ccgtggtgtt gtcggggaaa tcatcgtcct ttccttggct    7020
gctcgcctgt gttgccacct ggattctgcg cgggacgtcc ttctgctacg tcccttcggc    7080
cctcaatcca gcggaccttc cttcccgcgg cctgctgccg gctctgcggc ctcttccgcg    7140
tcttcgcctt cgccctcaga cgagtcggat ctccctttgg gccgcctccc cgcctggtac    7200
ctttaagacc aatgacttac aaggcagctg tagatcttag ccactttta aaagaaaagg     7260
ggggactgga agggctaatt cactcccaac gaaaataaga tctgcttttt gcttgtactg    7320
ggtctctctg gttagaccag atctgagcct gggagctctc tggctaacta gggaacccac    7380
tgcttaagcc tcaataaagc ttgccttgag tgcttcaagt agtgtgtgcc cgtctgttgt    7440
gtgactctgg taactagaga tccctcagac ccttttagtc agtgtggaaa atctctagca    7500
gtagtagttc atgtcatctt attattcagt atttataact tgcaaagaaa tgaatatcag    7560
agagtgagag gaacttgttt attgcagctt ataatggtta caaataaagc aatagcatca    7620
caaatttcac aaataaagca ttttttttcac tgcattctag ttgtggtttg tccaaactca   7680
tcaatgtatc ttatcatgtc tggctctagc tatcccgccc ctaactccgc ccagttccgc    7740
ccattctccg ccccatggct gactaatttt ttttatttat gcagaggccg aggccgcctc    7800
ggcctctgag ctattccaga agtagtgagg aggcttttt ggaggcctag acttttgcag     7860
agacggccca aattcgtaat catggtcata gctgtttcct gtgtgaaatt gttatccgct    7920
cacaattcca cacaacatac gagccggaag cataaagtgt aaagcctggg gtgcctaatg    7980
agtgagctaa ctcacattaa ttgcgttgcg ctcactgccc gctttccagt cgggaaacct    8040
gtcgtgccag ctgcattaat gaatcggcca acgcgcgggg agaggcggtt tgcgtattgg    8100
gcgctcttcc gcttcctcgc tcactgactc gctgcgctcg tcgttcggc tgcggcgagc     8160
ggtatcagct cactcaaagg cggtaatacg ttatccaca gaatcagggg ataacgcagg     8220
aaagaacatg tgagcaaaag gccagcaaaa ggccaggaac cgtaaaaagg ccgcgttgct    8280
ggcgtttttc cataggctcc gcccccctga cgagcatcac aaaaatcgac gctcaagtca    8340
gaggtggcga aacccgacag gactataaag ataccaggcg tttccccctg gaagctccct    8400
```

```
cgtgcgctct cctgttccga ccctgccgct taccggatac ctgtccgcct ttctcccttc    8460
gggaagcgtg gcgctttctc atagctcacg ctgtaggtat ctcagttcgg tgtaggtcgt    8520
tcgctccaag ctgggctgtg tgcacgaacc ccccgttcag cccgaccgct gcgccttatc    8580
cggtaactat cgtcttgagt ccaacccggt aagacacgac ttatcgccac tggcagcagc    8640
cactggtaac aggattagca gagcgaggta tgtaggcggt gctacagagt tcttgaagtg    8700
gtggcctaac tacggctaca ctagaaggac agtatttggt atctgcgctc tgctgaagcc    8760
agttaccttc ggaaaaagag ttggtagctc ttgatccggc aaacaaacca ccgctggtag    8820
cggtggtttt tttgtttgca agcagcagat tacgcgcaga aaaaaggat ctcaagaaga    8880 tcctttgatc ttttctacgg ggtctgacgc tcagtggaac gaaaactcac gttaagggat    8940
tttggtcatg agattatcaa aaaggatctt cacctagatc cttttaaatt aaaaatgaag    9000
ttttaaatca atctaaagta tatatgagta aacttggtct gacagttacc aatgcttaat    9060
cagtgaggca cctatctcag cgatctgtct atttcgttca tccatagttg cctgactccc    9120
cgtcgtgtag ataactacga tacgggaggg cttaccatct ggccccagtg ctgcaatgat    9180
accgcgagac ccacgctcac cggctccaga tttatcagca ataaaccagc cagccggaag    9240
ggccgagcgc agaagtggtc ctgcaacttt atccgcctcc atccagtcta ttaattgttg    9300
ccgggaagct agagtaagta gttcgccagt taatagtttg cgcaacgttg ttgccattgc    9360
tacaggcatc gtggtgtcac gctcgtcgtt tggtatggct tcattcagct ccggttccca    9420
acgatcaagg cgagttacat gatcccccat gttgtgcaaa aaagcggtta gctccttcgg    9480
tcctccgatc gttgtcagaa gtaagttggc cgcagtgtta tcactcatgg ttatggcagc    9540
actgcataat tctcttactg tcatgccatc cgtaagatgc ttttctgtga ctggtgagta    9600
ctcaaccaag tcattctgag aatagtgtat gcggcgaccg agttgctctt gcccggcgtc    9660
aatacgggat aataccgcgc cacatagcag aactttaaaa gtgctcatca ttggaaaacg    9720
ttcttcgggg cgaaaactct caaggatctt accgctgttg agatccagtt cgatgtaacc    9780
cactcgtgca cccaactgat cttcagcatc ttttactttc accagcgttt ctgggtgagc    9840
aaaaacagga aggcaaaatg ccgcaaaaaa gggaataagg gcgacacgga aatgttgaat    9900
actcatactc ttccttttc aatattattg aagcatttat cagggttatt gtctcatgag    9960
cggatacata tttgaatgta tttagaaaaa taaacaaata ggggttccgc gcacatttcc   10020
ccgaaaagtg ccacctgacg tctaagaaac cattattatc atgacattaa cctataaaaa   10080
taggcgtatc acgaggccct ttcgtctcgc gcgtttcggt gatgacggtg aaaacctctg   10140
acacatgcag ctcccggaga cggtcacagc ttgtctgtaa gcggatgccg ggagcagaca   10200
agcccgtcag ggcgcgtcag cgggtgttgg cgggtgtcgg gctggctta actatgcggc   10260 atcagagcag attgtactga gagtgcacca tatgcggtgt gaaataccgc acagatgcgt   10320
aaggagaaaa taccgcatca ggcgccattc gccattcagg ctgcgcaact gttgggaagg   10380
gcgatcggtg cgggcctctt cgctattacg ccagctggcg aaagggggat gtgctgcaag   10440
gcgattaagt tgggtaacgc cagggttttc ccagtcacga cgttgtaaaa cgacggccag   10500
tgccaagctg                                                         10510

<210> SEQ ID NO 6
<211> LENGTH: 9496
<212> TYPE: DNA
<213> ORGANISM: Artificial Sequence
<220> FEATURE:
```

<223> OTHER INFORMATION: Synthetic

<400> SEQUENCE: 6

| | | | | | |
|---|---|---|---|---|---|
| acgcgtgtag | tcttatgcaa | tactcttgta | gtcttgcaac | atggtaacga | tgagttagca | 60 |
| acatgcctta | caaggagaga | aaaagcaccg | tgcatgccga | ttggtggaag | taaggtggta | 120 |
| cgatcgtgcc | ttattaggaa | ggcaacagac | gggtctgaca | tggattggac | gaaccactga | 180 |
| attgccgcat | tgcagagata | ttgtatttaa | gtgcctagct | cgatacaata | aacgggtctc | 240 |
| tctggttaga | ccagatctga | gcctgggagc | tctctggcta | actagggaac | ccactgctta | 300 |
| agcctcaata | aagcttgcct | tgagtgcttc | aagtagtgtg | tgcccgtctg | ttgtgtgact | 360 |
| ctggtaacta | gagatccctc | agacccttttt | agtcagtgtg | gaaaatctct | agcagtggcg | 420 |
| cccgaacagg | gacctgaaag | cgaaagggaa | accagagctc | tctcgacgca | ggactcggct | 480 |
| tgctgaagcg | cgcacggcaa | gaggcgaggg | gcggcgactg | gtgagtacgc | caaaaatttt | 540 |
| gactagcgga | ggctagaagg | agagagatgg | gtgcgagagc | gtcagtatta | agcgggggag | 600 |
| aattagatcg | cgatgggaaa | aaattcggtt | aaggccaggg | ggaaagaaaa | aatataaatt | 660 |
| aaaacatata | gtatgggcaa | gcagggagct | agaacgattc | gcagttaatc | ctggcctgtt | 720 |
| agaaacatca | gaaggctgta | gacaaatact | gggacagcta | caaccatccc | ttcagacagg | 780 |
| atcagaagaa | cttagatcat | tatataatac | agtagcaacc | ctctattgtg | tgcatcaaag | 840 |
| gatagagata | aaagacacca | aggaagcttt | agacaagata | gaggaagagc | aaaacaaaag | 900 |
| taagaccacc | gcacagcaag | cggccactga | tcttcagacc | tggaggagga | gatatgaggg | 960 |
| acaattggag | aagtgaatta | tataaatata | aagtagtaaa | aattgaacca | ttaggagtag | 1020 |
| cacccaccaa | ggcaaagaga | agagtggtgc | agagagaaaa | aagagcagtg | ggaataggag | 1080 |
| ctttgttcct | tgggttcttg | ggagcagcag | gaagcactat | gggcgcagcc | tcaatgacgc | 1140 |
| tgacggtaca | ggccagacaa | ttattgtctg | gtatagtgca | gcagcagaac | aatttgctga | 1200 |
| gggctattga | ggcgcaacag | catctgttgc | aactcacagt | ctggggcatc | aagcagctcc | 1260 |
| aggcaagaat | cctggctgtg | gaaagatacc | taaaggatca | acagctcctg | ggatttggg | 1320 |
| gttgctctgg | aaaactcatt | tgcaccactg | ctgtgccttg | gaatgctagt | tggagtaata | 1380 |
| aatctctgga | acagattgga | atcacacgac | ctggatggag | tgggacagag | aaattaacaa | 1440 |
| ttacacaagc | ttaatacact | ccttaattga | agaatcgcaa | aaccagcaag | aaaagaatga | 1500 |
| acaagaatta | ttggaattag | ataaatgggc | aagtttgtgg | aattggttta | acataacaaa | 1560 |
| ttggctgtgg | tatataaaat | tattcataat | gatagtagga | ggcttggtag | gtttaagaat | 1620 |
| agttttttgct | gtactttcta | tagtgaatag | agttaggcag | ggatattcac | cattatcgtt | 1680 |
| tcagacccac | ctcccaaccc | cgaggggacc | cgacaggccc | gaaggaatag | aagaagaagg | 1740 |
| tggagagaga | gacagagaca | gatccattcg | attagtgaac | ggatctcgac | ggttaacttt | 1800 |
| taaaagaaaa | gggggggattg | gggggtacag | tgcaggggaa | agaatagtag | acataatagc | 1860 |
| aacagacata | caaactaaag | aattacaaaa | acaaattaca | aaaattcaaa | attttatcga | 1920 |
| tacaggaatt | ctggcgtgca | gtgggcgact | cagaaacgcc | caaaggtgct | cccccgagac | 1980 |
| aagcggtcgg | actaccatgg | aaatgccagg | acctcagcct | ctgggaagcg | ttaggaggtt | 2040 |
| aaaagagatg | agatcccttc | taaagggctg | gagaagatgt | cagtccaggt | aggactaatg | 2100 |
| gaaactttat | cgcggttcca | ggggcctcgg | cccgactgag | ctgggagggg | ccggaagct | 2160 |
| gggagtctgg | atgaggacg | aagttggagg | tgatggagg | tgggtgggca | gaccgcagct | 2220 |
| cctgggcaga | caagttcagg | aaggacagcc | gttggggccg | ttggatactg | ggagctggcg | 2280 |

```
ctccgccctc ttccctctca tccccccacc cgcgcctccc accaccgtcg gcggccctg    2340 cgcgtgcgcg cgcgcagaca ccggttgcca aacattgcat catccccgcc ccccgtcatc    2400
cctccctcgc cgcactctcc ttcgcccgcc cgcgcgcgcg cgcgcgcgcg cgcgcgcatg    2460
actcactcac ctcctccgcg gagcctcgtg acccaaagcc acttccgggt ccaagacaac    2520
gtagctctcc agccagaggg cggggcggag gcggggccg aggggctcc tgagtggcgg    2580 atgtaggggt gggcggagt cagtgccagc gtgccgcttt ctgattggca ggctcctggg    2640
tcccgccccc caaagagggg acgggcccg cataaaatat cttctctcgg cgctgcagag    2700
gtcagacgaa gtgtgagact caggctacgt ctagagctag cgccgccacc atggccgatg    2760
ctaagaacat taagaagggc cctgctccct tctaccctct ggaggatggc accgctggcg    2820
agcagctgca caaggccatg aagaggtatg ccctggtgcc tggcaccatt gccttcaccg    2880
atgcccacat tgaggtggac atcacctatg ccgagtactt cgagatgtct gtgcgcctgg    2940
ccgaggccat gaagaggtac ggcctgaaca ccaaccaccg catcgtggtg tgctctgaga    3000
actctctgca gttcttcatg ccagtgctgg gcgccctgtt catcggagtg gccgtggccc    3060
ctgctaacga catttacaac gagcgcgagc tgctgaacag catgggcatt tctcagccta    3120
ccgtggtgtt cgtgtctaag aagggcctgc agaagatcct gaacgtgcag aagaagctgc    3180
ctatcatcca gaagatcatc atcatggact ctaagaccga ctaccagggc ttccagagca    3240
tgtacacatt cgtgacatct catctgcctc ctggcttcaa cgagtacgac ttcgtgccag    3300
agtctttcga cagggacaaa accattgccc tgatcatgaa cagctctggg tctaccggcc    3360
tgcctaaggg cgtggccctg cctcatcgca ccgcctgtgt gcgcttctct cacgcccgcg    3420
accctatttt cggcaaccag atcatccccg acaccgctat tctgagcgtg gtgccattcc    3480
accacggctt cggcatgttc accaccctgg gctacctgat ttgcggcttt cgggtggtgc    3540
tgatgtaccg cttcgaggag gagctgttcc tgcgcagcct gcaagactac aaaattcagt    3600
ctgccctgct ggtgccaacc ctgttcagct tcttcgctaa gagcaccctg atcgacaagt    3660
acgacctgtc taacctgcac gagattgcct ctggcggcgc cccactgtct aaggaggtgg    3720
gcgaagccgt ggccaagcgc tttcatctgc caggcatccg ccaggctac ggcctgaccg    3780 agacaaccag cgccattctg attaccccag agggcgacga caagcctggc gccgtgggca    3840
aggtggtgcc attcttcgag gccaaggtgg tggacctgga caccggcaag accctgggag    3900
tgaaccagcg cggcgagctg tgtgtgcgcg gccctatgat tatgtccggc tacgtgaata    3960
accctgaggc cacaaacgcc ctgatcgaca aggacggctg gctgcactct ggcgacattg    4020
cctactggga cgaggacgag cacttcttca tcgtggaccg cctgaagtct ctgatcaagt    4080
acaagggcta ccaggtggcc ccagccgagc tggagtctat cctgctgcag cacccctaaca    4140 ttttcgacgc cggagtggcc ggcctgcccg acgacgatgc cggcgagctg cctgccgccg    4200
tcgtcgtgct ggaacacggc aagaccatga ccgagaagga gatcgtggac tatgtggcca    4260
gccaggtgac aaccgccaag aagctgcgcg gcggagtggt gttcgtggac gaggtgccca    4320
agggcctgac cggcaagctg gacgcccgca agatccgcga gatcctgatc aaggctaaga    4380
aaggcggcaa gatcgccgtg taagaattcg aatttaaatg gatccgcggc cgcaaggatc    4440
tgcgatcgct ccggtgcccg tcagtgggca gagcgcacat cgcccacagt ccccgagaag    4500 ttgggggggag gggtcggcaa ttgaacgggt gcctagagaa ggtggcgcgg ggtaaactgg    4560
gaaagtgatg tcgtgtactg gctccgcctt tttcccgagg gtgggggaga accgtatata    4620
```

```
agtgcagtag tcgccgtgaa cgttcttttt cgcaacgggt tgccgccag aacacagctg    4680 aagcttcgag gggctcgcat ctctccttca cgcgcccgcc gccctacctg aggccgccat    4740
ccacgccggt tgagtcgcgt tctgccgcct cccgcctgtg gtgcctcctg aactgcgtcc    4800
gccgtctagg taagtttaaa gctcaggtcg agaccgggcc tttgtccggc gctcccttgg    4860
agcctaccta gactcagccg gctctccacg ctttgcctga ccctgcttgc tcaactctac    4920
gtctttgttt cgttttctgt tctgcgccgt tacagatcca agctgtgacc ggcgcctacg    4980
ctagatgacc gagtacaagc ccacggtgcg cctcgccacc cgcgacgacg tccccagggc    5040
cgtacgcacc ctcgccgccg cgttcgccga ctaccccgcc acgcgccaca ccgtcgatcc    5100
ggaccgccac atcgagcggg tcaccgagct gcaagaactc ttcctcacgc gcgtcgggct    5160
cgacatcggc aaggtgtggg tcgcggacga cggcgccgcg gtggcggtct ggaccacgcc    5220
ggagagcgtc gaagcggggg cggtgttcgc cgagatcggc ccgcgcatgg ccgagttgag    5280
cggttcccgg ctggccgcgc agcaacagat ggaaggcctc ctggcgccgc accggcccaa    5340
ggagcccgcg tggttcctgg ccaccgtcgg cgtctcgccc gaccaccagg caagggtct    5400 gggcagcgcc gtcgtgctcc cggagtggga ggcggccgag cgcgccgggg tgccgccctt    5460
cctggagacc tccgcgcccc gcaacctccc cttctacgag cggctcggct tcaccgtcac    5520
cgccgacgtc gaggtgcccg aaggaccgcg cacctggtgc atgacccgca agcccggtgc    5580
ctgagtcgac aatcaacctc tggattacaa aatttgtgaa agattgactg gtattcttaa    5640
ctatgttgct ccttttacgc tatgtggata cgctgcttta atgcctttgt atcatgctat    5700
tgcttcccgt atggctttca ttttctcctc cttgtataaa tcctggttgc tgtctcttta    5760
tgaggagttg tggcccgttg tcaggcaacg tggcgtggtg tgcactgtgt ttgctgacgc    5820 aaccccact ggttggggca ttgccaccac ctgtcagctc ctttccggga ctttcgcttt    5880 cccctccct attgccacgg cggaactcat cgccgcctgc cttgcccgct gctggacagg    5940
ggctcggctg ttgggcactg acaattccgt ggtgttgtcg gggaaatcat cgtccttttcc    6000 ttggctgctc gcctgtgttg ccacctggat tctgcgcggg acgtccttct gctacgtccc    6060
ttcggccctc aatccagcgg accttccttc ccgcggcctg ctgccggctc tgcggcctct    6120
tccgcgtctt cgccttcgcc ctcagacgag tcggatctcc ctttgggccg cctccccgcc    6180
tggtaccttt aagaccaatg acttacaagg cagctgtaga tcttagccac ttttttaaaag    6240 aaaaggggg actggaaggg ctaattcact cccaacgaaa ataagatctg cttttgctt    6300 gtactgggtc tctctggtta gaccagatct gagcctggga gctctctggc taactaggga    6360
acccactgct taagcctcaa taaagcttgc cttgagtgct tcaagtagtg tgtgcccgtc    6420
tgttgtgtga ctctggtaac tagagatccc tcagaccctt ttagtcagtg tggaaaatct    6480
ctagcagtag tagttcatgt catcttatta ttcagtattt ataacttgca aagaaatgaa    6540
tatcagagag tgagaggaac ttgtttattg cagcttataa tggttacaaa taaagcaata    6600
gcatcacaaa tttcacaaat aaagcatttt tttcactgca ttctagttgt ggtttgtcca    6660
aactcatcaa tgtatcttat catgtctggc tctagctatc ccgcccctaa ctccgcccag    6720
ttccgcccat tctccgcccc atggctgact aatttttttt atttatgcag aggccgaggc    6780
cgcctcggcc tctgagctat tccagaagta gtgaggaggc ttttttggag gcctagactt    6840
ttgcagagac ggcccaaatt cgtaatcatg gtcatagctg tttcctgtgt gaaattgtta    6900
tccgctcaca attccacaca acatacgagc cggaagcata aagtgtaaag cctgggtgc    6960 ctaatgagtg agctaactca cattaattgc gttgcgctca ctgcccgctt tccagtcggg    7020
```

```
aaacctgtcg tgccagctgc attaatgaat cggccaacgc gcggggagag gcggtttgcg    7080
tattgggcgc tcttccgctt cctcgctcac tgactcgctg cgctcggtcg ttcggctgcg    7140
gcgagcggta tcagctcact caaaggcggt aatacggtta tccacagaat cagggataa     7200 cgcaggaaag aacatgtgag caaaaggcca gcaaaaggcc aggaaccgta aaaaggccgc    7260
gttgctggcg ttttccata  ggctccgccc ccctgacgag catcacaaaa atcgacgctc    7320
aagtcagagg tggcgaaacc cgacaggact ataaagatac caggcgtttc ccctggaag    7380 ctccctcgtg cgctctcctg ttccgaccct gccgcttacc ggatacctgt ccgcctttct    7440
cccttcggga agcgtggcgc tttctcatag ctcacgctgt aggtatctca gttcggtgta    7500
ggtcgttcgc tccaagctgg gctgtgtgca cgaacccccc gttcagcccg accgctgcgc    7560
cttatccggt aactatcgtc ttgagtccaa cccggtaaga cacgacttat cgccactggc    7620
agcagccact ggtaacagga ttagcagagc gaggtatgta ggcggtgcta cagagttctt    7680
gaagtggtgg cctaactacg gctacactag aaggacagta tttggtatct gcgctctgct    7740
gaagccagtt accttcggaa aaagagttgg tagctcttga tccggcaaac aaaccaccgc    7800
tggtagcggt ggtttttttg tttgcaagca gcagattacg cgcagaaaaa aaggatctca    7860
agaagatcct ttgatctttt ctacggggtc tgacgctcag tggaacgaaa actcacgtta    7920
agggattttg gtcatgagat tatcaaaaag gatcttcacc tagatccttt taaattaaaa    7980
atgaagtttt aaatcaatct aaagtatata tgagtaaact tggtctgaca gttaccaatg    8040
cttaatcagt gaggcaccta tctcagcgat ctgtctattt cgttcatcca tagttgcctg    8100
actccccgtc gtgtagataa ctacgatacg ggagggctta ccatctggcc ccagtgctgc    8160
aatgataccg cgagacccac gctcaccggc tccagattta tcagcaataa accagccagc    8220
cggaagggcc gagcgcagaa gtggtcctgc aactttatcc gcctccatcc agtctattaa    8280
ttgttgccgg gaagctagag taagtagttc gccagttaat agtttgcgca acgttgttgc    8340
cattgctaca ggcatcgtgg tgtcacgctc gtcgtttggt atggcttcat tcagctccgg    8400
ttcccaacga tcaaggcgag ttacatgatc ccccatgttg tgcaaaaaag cggttagctc    8460
cttcggtcct ccgatcgttg tcagaagtaa gttggccgca gtgttatcac tcatggttat    8520
ggcagcactg cataattctc ttactgtcat gccatccgta agatgctttt ctgtgactgg    8580
tgagtactca accaagtcat tctgagaata gtgtatgcgg cgaccgagtt gctcttgccc    8640
ggcgtcaata cgggataata ccgcgccaca tagcagaact ttaaaagtgc tcatcattgg    8700
aaaacgttct cggggcgaaa actctcaag  gatcttaccg ctgttgagat ccagttcgat    8760
gtaacccact cgtgcaccca actgatcttc agcatctttt actttcacca gcgtttctgg    8820
gtgagcaaaa acaggaaggc aaaatgccgc aaaaaaggga ataagggcga cacggaaatg    8880
ttgaatactc atactcttcc tttttcaata ttattgaagc atttatcagg gttattgtct    8940
catgagcgga tacatatttg aatgtattta gaaaaataaa caataggggt tccgcgcac     9000 atttccccga aaagtgccac ctgacgtcta agaaaccatt attatcatga cattaaccta    9060
taaaaatagg cgtatcacga ggccctttcg tctcgcgcgt ttcggtgatg acggtgaaaa    9120
cctctgacac atgcagctcc cggagacggt cacagcttgt ctgtaagcgg atgccgggag    9180
cagacaagcc cgtcagggcg cgtcagcggg tgttggcggg tgtcggggct ggcttaacta    9240
tgcggcatca gagcagattg tactgagagt gcaccatatg cggtgtgaaa taccgcacag    9300
atgcgtaagg agaaaatacc gcatcaggcg ccattcgcca ttcaggctgc gcaactgttg    9360
```

```
ggaagggcga tcggtgcggg cctcttcgct attacgccag ctggcgaaag ggggatgtgc    9420
tgcaaggcga ttaagttggg taacgccagg gttttcccag tcacgacgtt gtaaaacgac    9480
ggccagtgcc aagctg                                                    9496
```

VITRO METHOD FOR HIGH THROUGHPUT SCREENING OF GENOTOXIC AGENTS IN EUKARYOTIC CELLS

TECHNICAL FIELD

The present invention relates generally to the field of molecular biology and toxicology and specifically to molecular engineered cell line with multi component reporter system for the detection of DNA damage. The present invention also has an immediate relevance to the field of drug discovery and serves as a filter for potential drugs with off target genotoxic effects.

BACKGROUND ART

Genotoxicity is generally defined as any damage to the integrity of a cell's DNA caused either directly through chemical interaction with DNA, or indirectly through interference with the cell's structural or enzymatic machinery, that has potential to lead to an inheritable defect in the genetic information carried by that cell. The genotoxicity or DNA damage can be caused by variety of agents such as ultraviolet light, X-Rays, free radicals, methylating agents and other mutagenic compounds. These DNA damaging agents are known as genotoxins. In microorganisms such mutations may lead to the evolution of new undesirable strains of the microorganism. For instance, antibiotic or herbicide resistant bacteria may arise. In animals these mutations can lead to carcinogenesis or may damage the gametes to give rise to congenital defects in offspring.

Thus, these DNA damaging agents chemically modify the nucleotides that comprise DNA and may also break the phosphodiester bonds that link the nucleotides or disrupt association between bases (T-A or C-G). To counter the effect of these DNA damaging agents, cells have evolved number of mechanisms. For instance, the SOS response in *E. coli* is a well-characterized cellular response induced by DNA damage in which a series of proteins are expressed, including DNA repair enzymes, which repair the damaged DNA. The eukaryotic cells also exhibit mechanisms such as nucleotide excision repair, base excision repair, non-homologous end-joining, homologous recombination and cell cycle arrest to allow DNA repair.

Therefore, it is important to identify which agents cause or potentiate DNA damage. For instance, a method of detecting these agents may be used as a mutagenesis assay for screening compounds that are candidate medicaments, food additives or cosmetics to assess whether or not the compound of interest induces DNA damage. Alternatively, methods of detecting DNA damaging agents may be used to monitor contamination of water supplies with pollutants that contain mutagenic compounds.

Majority of the genotoxicity assays used for regulatory toxicity testing were developed in 1970's. Their throughput could not meet the requirements of the present drug discovery requirements (Krishna et al., 1998). In most of the cases, the site and mechanism by which genotoxicity is produced by the compound under the study is not known. It may happen that the target site in the test system may not be the same target site of toxic action of the new chemical entities.

Currently there are varieties of in vitro and in vivo assays to detect genotoxicity. In vitro assays include Ames test, in vitro micronucleus test, in vitro chromosomal aberration test, comet assays and mouse lymphoma assay. In vivo assays involve the measurement of the size of a tumor mass in animal models when exposed to drugs. All these above-mentioned assays require incubating the samples from several days to weeks, whereas, it is often desirable to obtain genotoxic data in a shorter time frame. The assays such as 'Ames test' consider the lasting DNA damage as an endpoint (either the mutated DNA or unrepaired damage in the form of fragmented DNA). However, such conditions occur only in severe cases where repair mechanism is exhausted. In most occasions, the DNA damage is repaired before such an endpoint can be measured. Hence such assays are time consuming and relatively less sensitive. Also, the involvement of animals even for the preliminary screen warrants an immediate requirement to design and implement novel tools that filter out genotoxic entities.

Some short term methods are also available for screening genotoxic compounds, such as umu test and SOS chromotest. In the umu test and SOS chromotest the host microorganism is cultured in the presence of the sample to be tested and subsequently the host microorganism is disrupted. These tests overcome the long timespan problem of the Ames test; however they have their own disadvantages. The sensitivity is low and in particular the detection sensitivity of nitroarenes and polycyclic aromatic hydrocarbons is low. In addition the detection method requires a large number of actions and additions of various reagents thereby rendering the method complicated and expensive. Due to the fact that the cell has to be disrupted in order to carry out detection of any induction it is only possible to carry out one measurement on the cell.

Exposure of cells to genotoxic agents results in the regulation of number of damage response genes. The change in the expression of such genes upon DNA damage can hence be used to develop assays that detect early genotoxic responses in the cell. Among the well characterized events induced by genotoxic stress is the activation of p53 signaling pathway. The tumor suppressor gene p53 maintains genomic stability by inducing cell cycle arrest through activation of the cyclin-dependent kinase inhibitor p21WAF1/Cip1gene promoter as an early response to DNA damage. It has been suggested that p53 activates expression of its target genes such as p21WAF1/Cip1 and GADD by multiple but perhaps interrelated mechanisms.

Treatment of mammalian cells with genotoxic agents causes an increase in the mRNA levels of a number of 'damage response' genes (reviewed by Holbrook and Fornace). Many of these genes are also inducible by phorbol ester treatment. Among those that do not respond to phorbol ester treatment, some can be activated by the tumor suppressor gene p53, such as WAF1 and GADD45. However, there are also a number of DNA damage inducible genes for which the activation signal is unknown, and GADD153 is one of these genes. GADD153 is of particular interest because the magnitude of the increase in GADD153 mRNA following cellular injury is greater than most other 'damage response' genes.

GADD153 was originally cloned by subtractive hybridization of W-treated versus proliferating Chinese hamster ovary cells. The GADD153 gene was one of a subset of genes that was induced by UV-radiation and other forms of DNA damage, but not by heatshock or phorbol ester treatment. This subset of genes was found to be coordinately regulated by a number of agents that damage DNA or induce cell cycle arrest. GADD153 is highly conserved among mammalian species; hamster GADD153 shares 78% nucleotide sequence identity with the human exons (Park et al., 1992) and >85% with the mouse exons (Ron and Habener, 1992). Gadd153 is induced by DNA damaging agents in cells with mutant or absent p53 and the induction is greater in p53 wt cells (Hollander and Fornace, 1995). It has been shown previously that hamster GADD153 gene promoter over expressed in mammalian cells showed better relative fold induction when treated with MMS and TPA (Luethy et al., 1990).

U.S. Pat. No. 6,344,324 discloses a recombinant DNA molecule comprising the regulatory element of the hamster GADD153 upstream promoter region that activates gene expression in response to a wide range of cellular stress conditions, linked to a DNA sequence that encodes GFP (Green Fluorescent Protein). This reporter system is carried out in a human head and neck squamous-cell carcinoma cell line. However, problems associated with this reporter system are that it requires at least a four day treatment period at test agent concentrations that result in less than 10% cell survival, followed by analysis of fluorescence by flow cytometry. In addition, the biological relevance of any gene induction when tested with agents at this level of toxicity is debatable. Furthermore, this development does not disclose a means of specifically monitoring the presence of agents that may cause or potentiate DNA damage, and the mechanism of GADD153 induction remains unclear. Hence, this system is of very limited use as a human DNA damage biosensor.

Another patent, WO2010/112821 discloses a DNA sequence encoding Gaussia luciferase (GLuc) reporter protein which is operatively linked to a human GADD45a gene promoter and a human GADD45α gene regulatory element. This is designed to activate expression of the DNA sequence encoding Gaussia luciferase (GLuc) reporter protein in response to genome damage. The advantage of this system is that it does not require the lysis of cells during the assay as GLuc is secretory. An advantage of using luminescence as a reporter assay is that there is no need for the incident light, as required in fluorescence based assays. Hence, unwanted fluorescence can be avoided that would otherwise mask the signal from the GFP reporter protein. The use of luminescence therefore permits screening colored and fluorescent test compounds. The above mentioned assays are limited to being a screen capable of identifying test compounds that trigger a particular DNA damage response pathway.

For the foregoing reasons, there is a need for high throughput in vitro assay which can detect wide range of genotoxins in eukaryotic mammalian cells, by retaining the simplicity associated with chemiluminescent assay. The present invention employs three genotoxicity early response gene promoters in a single cell which makes this invention more sensitive and efficient compared to other currently available assays.

DISCLOSURE OF INVENTION

Summary of the Invention

The present invention discloses the utilization of more than one type of DNA damage-response gene promoter to detect diverse genotoxic stress signaling events. The gene promoters are stably expressed in mammalian cell lines and employ a lentiviral system to ectopically deliver the genes. Lentivirus-based stable cell line generation combines the superior efficiency of gene delivery with stable integration of the gene into the genome of the host.

According to a first aspect, this invention provides a three expression cassettes comprising a DNA sequence encoding reporter protein operatively linked to a gene promoter. The first expression cassette comprises DNA sequence encoding Renilla Luciferase (RLuc) and derivatives thereof as reporter protein, which is operatively linked to human p21 gene promoter. The second expression cassette comprises DNA sequence encoding humanized Firefly Luciferase (hFLuc) and derivatives thereof as reporter protein, which is operatively linked to hamster GADD153 gene promoter. The third expression cassette comprises DNA sequence encoding beta galactosidase (Bgal) and derivatives thereof as reporter protein, which is operatively linked to p53 response element and polyoma virus UTR as the promoter. The system is arranged in such a way to activate expression of DNA sequence encoding reporter protein in response to genome damage.

According to a second aspect, this invention provides recombinant vectors comprising the expression cassettes.

According to a third aspect, this invention provides a method for generation of a stable cell line to incorporate the recombinant vectors in accordance with the second aspect of the invention.

According to a fourth aspect, the invention provides a method for detecting the presence of genotoxic agent that causes or potentiates DNA damage comprising subjecting the cell line to a genotoxic agent and monitoring the expression of the light emitting reporter protein from the cell. The method for the screening of genotoxic compounds according to the fourth aspect represents a novel cost-effective, high throughput, rapid genotoxicity assay that may be used to provide a pre-regulatory screening of compounds for pharmaceutical industries or other areas that require testing agents for genotoxicity. Furthermore, the screening of genotoxic compounds can also be carried out in the presence of liver microsomes or S9 fraction as its addition increases the sensitivity of determining the progenotoxins or metabolically active genotoxic compounds. The present invention describes a high throughput assay that has a lower compound consumption than existing in vitro and in vivo mammalian genotoxicity assays, and is sensitive to a wide range of genotoxins.

BRIEF DESCRIPTION OF DRAWINGS

Description of Drawings

Figure 1:
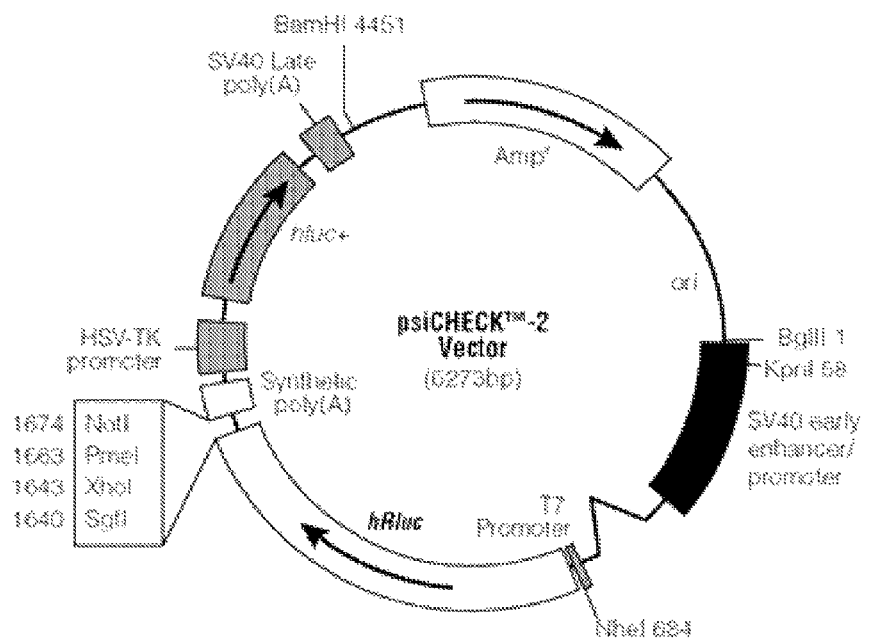
Figure 2:
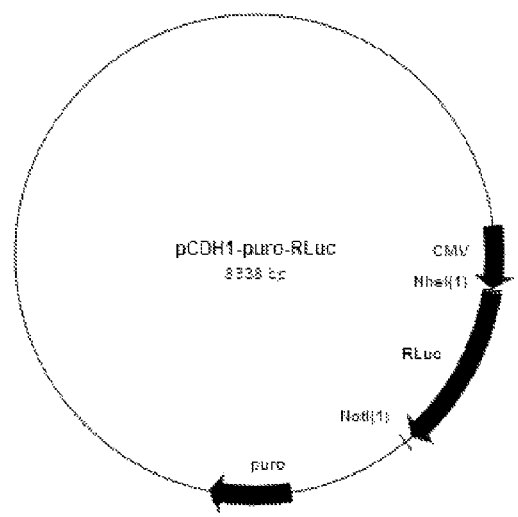
Figure 3:
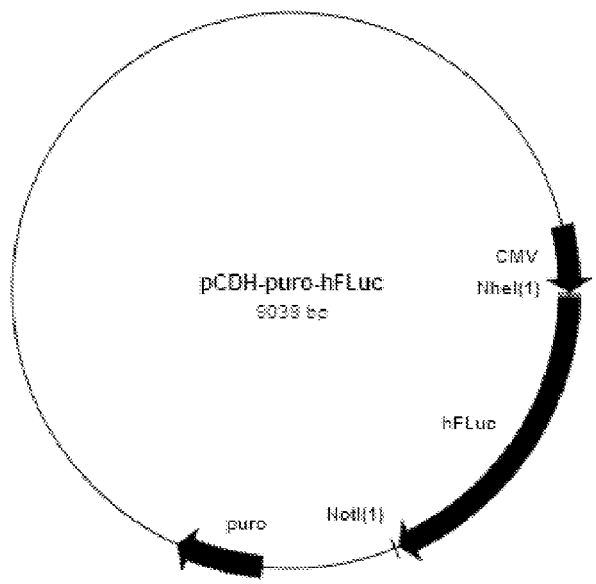
Figure 4:
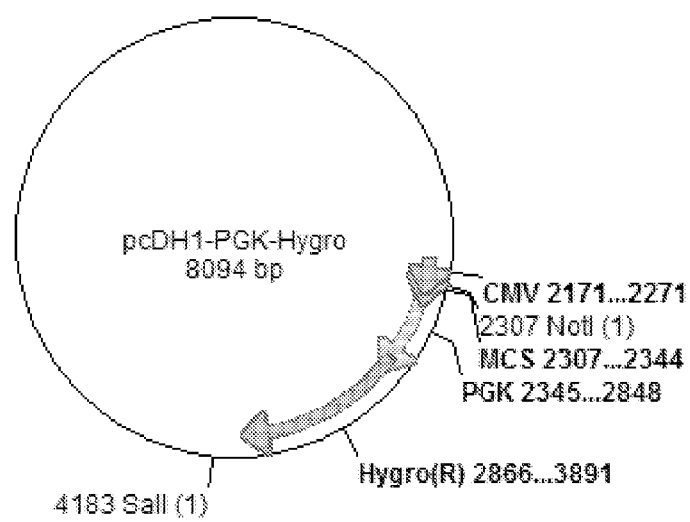
Figure 5:
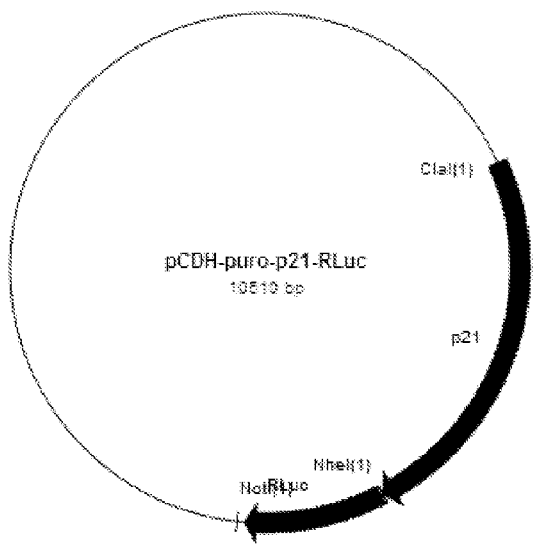
Figure 6:
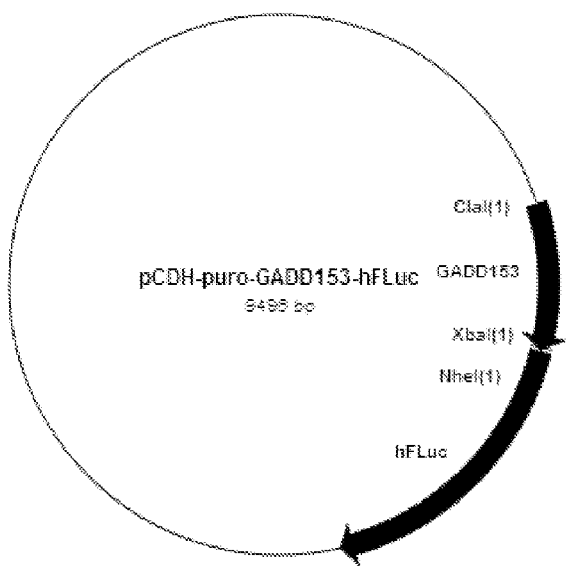
Figure 7:
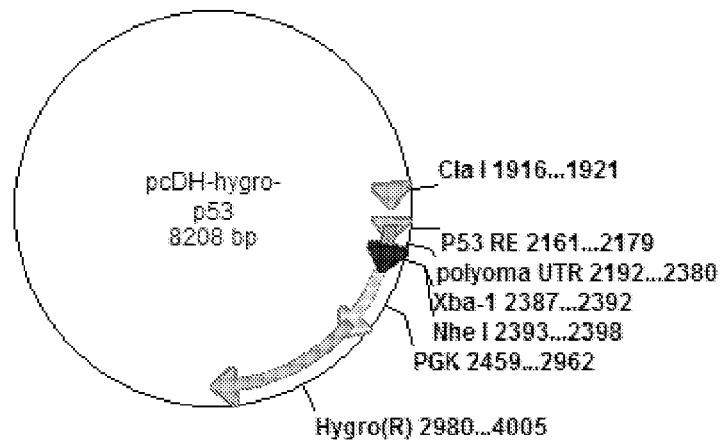

In accordance with the preferred embodiments of the present invention, FIG. 1 depicts restriction map of vector psiCHECK 2 from Promega containing RLuc and hFLuc In accordance with the preferred embodiments of the present invention, FIG. 2 depicts restriction map of vector pCDH puro-RLuc In accordance with the preferred embodiments of the present invention, FIG. 3 depicts restriction map of vector pCDH puro-hFLuc In accordance with the preferred embodiments of the present invention, FIG. 4 depicts restriction map of vector pCDH CMV-MCS-PGK-hygro In accordance with the preferred embodiments of the present invention, FIG. 5 depicts restriction map of vector pCDH puro-p21-RLuc In accordance with the preferred embodiments of the present invention, FIG. 6 depicts restriction map of vector pCDH puro-GADD153-hFLuc In accordance with the preferred embodiments of the present invention, FIG. 7 depicts restriction map of vector pCDH-hygro-p53

Figure 8:
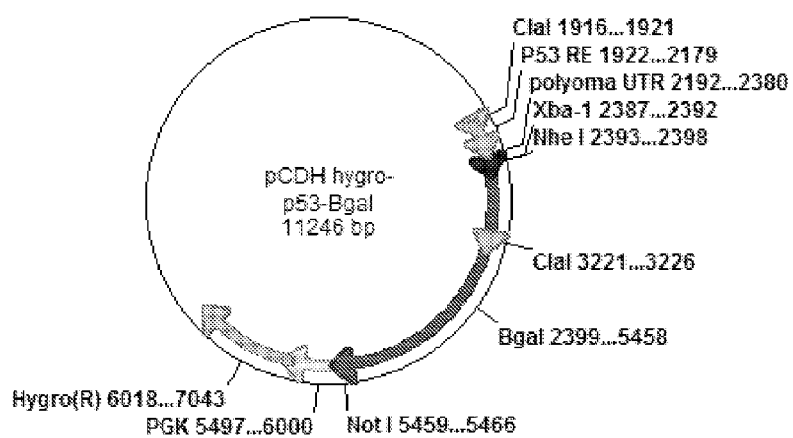
Figure 9:
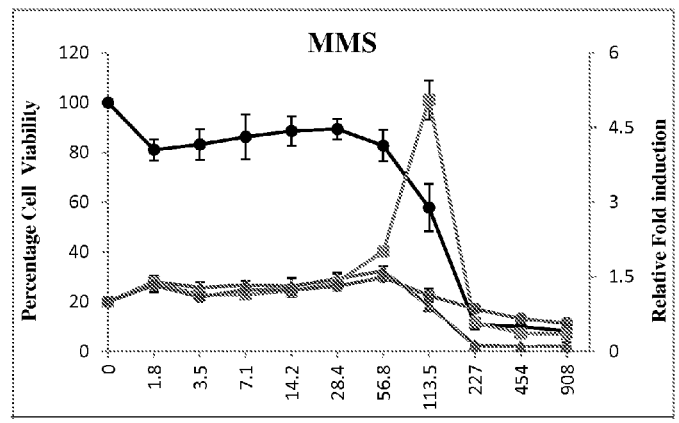

In accordance with the preferred embodiments of the present invention, FIG. 8 depicts restriction map of vector pCDH hygro-p53-Bgal In accordance with the preferred embodiments of the present invention, FIG. 9 depicts reporter induction and percentage cell viability of HCT116-p21RLuc-GADD153hFLuc-p53Bgal cells treated with different concentrations of, Methyl methanesulphonate (a direct acting genotoxin)

Figure 10:
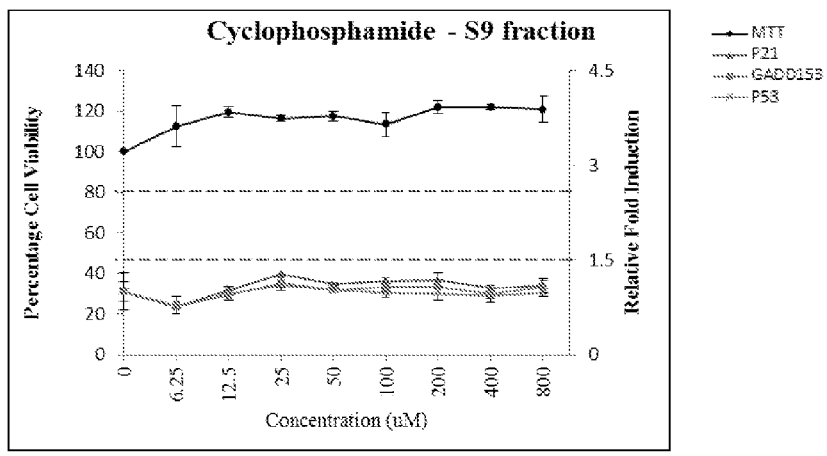
Figure 10:
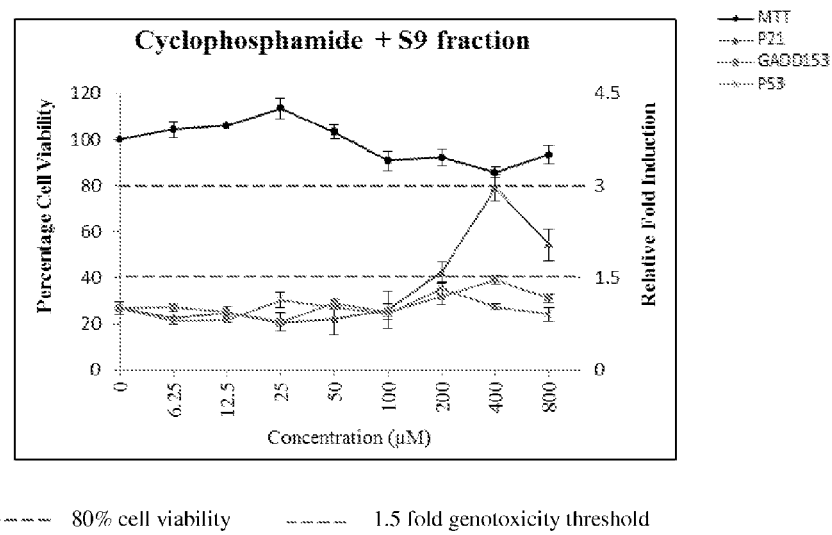

In accordance with the preferred embodiments of the present invention, FIG. 10A depicts reporter induction and percentage cell viability of HCT116-p21RLuc-GADD153hFLuc-p53Bgal cells treated with different concentrations of cyclophosphamide (a progenotoxin)

In accordance with the preferred embodiments of the present invention, FIG. 10B depicts reporter induction and percentage cell viability of HCT116-p21RLuc-GADD153hFLuc-p53Bgal cells treated with different concentrations of cyclophosphamide pretreated with S9 fraction.

In accordance with the preferred embodiments of the present invention Table 1 lists the compounds screened using Genotox assay.

BEST MODE FOR CARRYING OUT THE INVENTION

Best Mode

Unless otherwise defined, all technical and scientific terms used herein have the meaning commonly understood by a person skilled in the art to which this invention belongs. One skilled in the art will recognize many methods and materials similar or equivalent to those described herein, which could be used in the practice of this invention. Indeed, this invention is in no way limited to the methods and materials described. For clarity, the following definitions are used herein.

By the term 'operatively linked', we mean that the promoter is able to induce the expression of the respective reporter proteins in response to DNA damage.

By 'genome damage' we refer to DNA damage caused by agents that affect structural components of DNA (e.g. histones) including histone deacetylation inhibitors, the mechanisms of nuclear and cell division (e.g. spindle formation), or genome maintenance systems such as topoisomerases and polymerases and DNA repair systems any chemical modification of nucleotides, any insertion/deletion/replacement of nucleotides, alterations in chromosome numbers, and DNA synthesis.

By 'reporter protein' we refer to any nucleic acid sequence which, when expressed in a cell, causes the cell to display a detectable label, such as a fluorescent or phosphorescent signal, an enzyme activity detectable in an assay, or an antigen detectable on or in the cell by a specific stain, antibody, or lectin.

By the term 'Renilla luciferase (RLuc) reporter protein and derivatives thereof' we include a protein derived from the Renilla reniformis, Sea pansy which when expressed is detectable by a luciferase assay. Derivatives of RLuc include DNA sequences encoding for polypeptide analogues or polypeptide fragments of RLuc, which retain luminescent activity. Nucleic acid sequences encoding RLuc proteins are commercially available from a number of different companies; for example, PsiCHECK2 from Promega. The nucleotide sequence encoding such a protein can be obtained from a number of difference sources; for example GenBank accession number M63501.1

By the term 'Firefly luciferase (FLuc) reporter protein and derivatives thereof' we include a protein derived from the Photinus pyralis, the common eastern fly, which when expressed is detectable by a luciferase assay. Derivatives of FLuc include DNA sequences encoding for polypeptide analogues or polypeptide fragments of FLuc, which retain luminescent activity. Nucleic acid sequences encoding FLuc proteins are commercially available from a number of different companies; for example, PsiCHECK2 from Promega. Nucleotide sequence encoding such a protein can be obtained from a number of difference sources; for example GenBank accession number M15077.1.

By the term 'Beta Galactosidase (Bgal) reporter protein and derivatives thereof' we include a hydrolase enzyme that catalyses the hydrolysis of beta galactosides into monosaccharides. Nucleic acid sequences encoding Bgal proteins are commercially available from a number of different companies. The nucleotide sequence encoding such a protein can be obtained from a number of difference sources; for example GenBank accession number AF105229.1

The present invention provides utilization of multiple genotoxicity early response gene promoters in the same cell, which makes this invention more sensitive and efficient compared to other conventional genotoxicity assays. The test compounds used in our assay are very less luminescent hence less control reactions are required which means greater number of test compounds can be assayed in parallel. Though the bioluminescence assays can be performed using 384-well microtitre plates but these 384-well microtitre plates cannot be used for similar fluorescence-based reporter assays. If used, it contains reduced volume of assay liquid, which means reduced number of cells and hence poor 'signal to noise' ratio. Lower the 'signal to noise' ratio less sensitive is the testing system. Therefore the bioluminescence-based genotoxicity assay can be more readily used in higher throughput screening systems than with fluorescence-based assays.

Bioluminescence is a naturally occurring form of chemiluminescence where energy is released by a chemical reaction in the form of light emission. It is the production and emission of light by a living organism. There are many distinct classes of bioluminescence derived through separate evolutionary histories. These classes are widely divergent in their chemical properties, yet they all undergo similar chemical reactions, namely the formation and destruction of a dioxetane structure. The classes are all based on the interaction of the enzyme luciferase with a luminescent substrate luciferin. The luciferin reacts with oxygen to create light. The luciferase acts as a catalyst to speed up the reaction, which is sometimes mediated by cofactors such as calcium ions or ATP. Luciferase genes have been cloned from a very wide range of difference organisms, including, bacteria, beetles (e.g., firefly and click beetle), Renilla, Aequorea, Vargula and Gonyaulax (a dinoflagellate), and crustaceans. There are currently many different luciferase enzymes that are available for use in bioluminescent assays such as Renilla luciferase (RLuc), Firefly luciferase (FLuc). The Firefly luciferase (FLuc) is the most commonly used bioluminescent reporter protein.

In luminescent chemical reactions, light is produced by the oxidation of luciferin (pigment). For instance, Renilla luciferase (RLuc) reporter protein catalyses the oxidation of coelenterazine in a luminescent reaction:

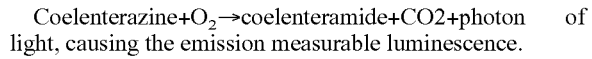
Coelenterazine+$O_2$→coelenteramide+$CO2$+photon of light, causing the emission measurable luminescence.

And, Firefly luciferase (FLuc) reporter protein catalyses the oxidation of luciferin in a chemical reaction producing light. Magnesium is required as co-factor in the reaction:

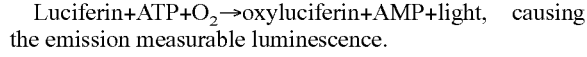
Luciferin+ATP+$O_2$→oxyluciferin+AMP+light, causing the emission measurable luminescence.

The beta galactosidase reporter gene activity can be measured using chemiluminiscent substrates such as Galacton-star. The beta-galactosidase cleaves a galactoside moiety from the substrate and an intermediate is produced that further degrades with the concurrent emission of light. This light emission provides a quantitative measure of Galacton-Star hydrolysis and beta-galactosidase activity. The beta galactosidase reporter gene activity can also be measured by absorbance at 420 nm using substrates such as o-nitrophenyl-β-D-galactopyraniside. When the β-galactosidase cleaves ONPG, o-nitrophenol is released. This compound has a yellow color, and absorbs 420 nm light. To measure β-galactosidase activity the accumulation of yellow color (increase 420 nm absorbance)/minute is monitored.

RLuc produces a high quantum yield of light, does not require ATP while FLuc requires ATP, both of these reporter proteins are detectable by commercially available luminometers. Since, RLuc and FLuc employ two different substrates and their light emission follows different time kinetics, they are ideal pairs in any dual reporter system. DNA molecules coding RLuc and FLuc reporter proteins may be used for detecting agents that cause or potentiate genome damage.

Nucleic acid sequence encoding a 'humanised' Renilla luciferase (hRLuc) reporter protein or humanized Firefly luciferase (hFLuc) are optimised for expression in human cell lines. There are a number of sources to obtain the same, for example: Cloning vector pGL3-Promoter (GenBank Accession Number U47298) or from Promega construct pRL-TK, pHGCX constructs containing either the hFLuc (1650 bp) or the hRLuc (933 bp) cDNA, both codon optimized for mammalian cell expression (Promega, Madison, Wis., USA).

Furthermore, the expression cassette comprising promoter-reporter system according to the first aspect of the invention is delivered through lentiviral system for the stable expression of the reporter protein in cell line. Stable single cell clones are generated to obtain a homogenous population of cells. Further, these cells may be subjected to the test agent or compound, and expression of the reporter protein in the cell indicates whether the test agent causes genome damage.

Accordingly, the present invention describes the use of three DNA, encoding a human p21, the hamster GADD153 and human p53 response elements (p53RE) with polyoma virus untraslated region (UTR) gene promoters operatively linked to three reporter proteins, RLuc, FLuc and Bgal, to form a cassette in accordance with the first aspect of the invention and then further used in a genotoxic test according to the fourth aspect of the invention.

Preferably, the human p21 gene promoter and/or the hamster GADD153 gene promoter and/or p53 response element sequences induce RNA polymerase to bind to the DNA molecule and start transcribing the DNA encoding the reporter proteins, Rluc and/or FLuc and/or Bgal. The promoter sequences of human p21 may be obtained from the pCDH-puro-p21-RLuc plasmid, which is illustrated in FIG. 5, hamster GADD153 is obtained from the pCDH-puro-GADD153-hFLuc plasmid, which is illustrated in FIG. 6 and human p53 is obtained from pCDH-hygro-p53-Bgal plasmid which is illustrated in FIG. 8. The nucleotide sequence of the human p21 gene promoter is shown as nucleotides 1961 to 4456 of SEQ ID NO: 2, that of hamster GADD 153 gene promoter is shown as 1961 to 2741 of SEQ ID NO: 3 and that of p53 response element with polyoma UTR is shown as 1932 to 2380 of SEQ ID NO: 7 in the sequence listing. The promoter may comprise each of the bases mentioned above or alternatively may be a functional derivative or functional fragment thereof. Functional derivatives and functional fragments may be readily identified by assessing whether or not transcriptase will bind to a putative promoter region and will then lead to the transcription of the marker protein. Alternatively such functional derivatives and fragments may be examined by conducting mutagenesis study on the aforesaid promoters.

Hence, preferred expression cassettes according to the first aspect of the invention comprise a human p21 gene promoter operatively linked to a DNA sequence encoding a Renilla luciferase (R Luc) reporter protein, hamster GADD153 gene promoter operatively linked to a DNA sequence encoding Firefly luciferase (F Luc) and human p53 response element with polyoma virus UTR promoter operatively linked to a DNA sequence encoding beta galactosidase (Bgal).

In accordance with the second aspect of the invention, the recombinant vector may be lentiviral vector, pCDH (System Biosciences). Such recombinant vectors are of great utility for generation of stable cell lines. Such replicating vectors can give rise to multiple copies of the DNA molecule in a transformant and are therefore useful during over-expression and thereby increased light emission of the Luc reporter proteins. It is preferred that the vector comprises at least one selectable marker. The selectable marker may confer resistance to an antibiotic, for example, puromycin, hygromycin or neomycin.

In a preferred embodiment, the recombinant vector is preferably pCDH-puro-p21-RLuc, pCDH-puro-GADD153-hFLuc and pCDH-hygro-p53-Bgal as illustrated in FIGS. 5,6 and 8.

In accordance with the third aspect of the present invention, the expression cassette or recombinant vector of the invention is incorporated within a cell. It is preferred that the cells may eukaryotic cells and cell lines. Preferred mammalian cells include human, primate, murine or canine cells. The host cells may be lymphoma cells or primary cells or cell lines, such as mouse lymphoma cells. While the inventors do not wish to be bound by any hypothesis, the inventors have found that HCT116 human colorectal carcinoma cells are particularly preferred cell lines for use according to the method of the invention.

Host cells used for expression of the protein encoded by the DNA molecule are ideally stably transfected, although the use of unstably transfected (transient) cells is not precluded. The transfected cells according to the third aspect of the invention may be formed by following procedures described in the Example. The cell is ideally a human cell line, for example HCT 116. Such stably transduced cells may be used according to the method of the fourth aspect of the invention to assess whether or not agents induce or potentiate DNA damage. RLuc and FLuc expressions are induced in response to DNA damage and the light emitted by RLuc and FLuc may be easily measured using known appropriate techniques. Most preferred cells according to the third aspect of the invention are HCT116 cells stably transduced by lentiviral system. These cells are referred to herein as HCT116-p21RLuc-GADD153FLuc-p53Bgal.

In accordance with the fourth aspect of the present invention, a method particularly useful for detecting agents that induce genome damage, at low concentrations is described. The method may be used as a mutagenesis assay to screen compounds used in food additives, candidate medicaments or cosmetics induce DNA damage. The method can also be used to assess whether it is safe to expose a living organisms, particularly humans, to such compounds. Alternatively, the method of the fourth aspect of the invention may be employed to detect genotoxins in water supplies and in the environment. For instance, the methods may be used to monitor industrial effluents for the presence of pollutants that may lead to increased genome damage in people or other organisms exposed to the pollution.

The method of the present invention is preferably performed by growing cells transfected with a recombinant vector according to the second aspect of the invention, incubating the cells with the agent which putatively causes genome damage for a pre-determined time and monitoring the activity of the RLuc and/or FLuc reporter and/or beta galactosidase proteins from the sample of treated cells. Suitable methods of luminescence/absorbance detection and quantitation will be known to the skilled technician, and a method is described in the examples.

According to a preferred embodiment of the method of the invention, luminescence readings may be recorded from HCT116-p21RLuc-GADD153FLuc-p53Bgal cell lysates following drug treatment in a microplate well. An example of a suitable microplate is a 96-well, white, clear-bottom sterile microplates (Nalgene Nunc catalogue no. 136101 is recommended for optimum performance). Luminescence and absorbance measurements may be recorded using a suitable microplate reader, for example, BioTek plate reader. Most preferred protocols for conducting the method of the fourth aspect of the invention are described in the accompanying example.

Preferred methods according to the fourth aspect of the invention will utilize cells according to the third aspect of the invention (e.g. HCT116-p21RLuc-GADD153FLuc-p53Bgal). Preferably in the method of the fourth aspect of the invention the expression of the RLuc, FLuc and Bgal reporter proteins are monitored after between 8 to 24 hours from exposure to the test compound; most preferably after 16 hours.

All of the features described herein (including any accompanying claims, abstract and drawings), and/or all of the steps of any method or process so disclosed, may be combined with any of the above aspects in any combination, except combinations where at least some of such features and/or steps are mutually exclusive.

In order that this invention be more fully understood, the following preparative and testing examples are set forth. These examples are for the purpose of illustration only and are not to be construed as limiting the scope of the invention in any way.

EXAMPLE 1

The following example illustrates the construction of HCT116-p21RLuc-GADD153FLuc-p53Bgal stable cell line to detect DNA damage according to the first, second and third aspects of the invention. In addition it also outlines how this stable cell line is used to test a genotoxic agent, for example Etoposide when used according to the method described in the fourth aspect of this invention.

Components of this system:
1) The promoters—human p21, hamster GADD153 and human p53
2) The reporter genes—Renilla Luciferase (RLuc), Firefly Luciferase (FLuc) and Beta Galactosidase (Bgal)

Construction of the Lentivectors encoding the Biosensor Reporter casettes:

Step 1: Cloning of the Reporter Proteins—Renilla Luciferase (RLuc), Firefly Luciferase (FLuc).

The source of the RLuc is pSiCHECK2 (Promega), which is shown in FIG. 1. The RLuc was flanked by Nhe I (5') and Not I (3') sites. This was inserted into the vector pCDH-CMV-MCS-EF1-puro (from System Biosciences) and the resulting plasmid was called pCDH-puro-RLuc, which is shown in FIG. 2. The FLuc was amplified by PCR from pSiCHECK2 (Promega), which is shown in FIG. 1. The sequence of the primers is shown in sequence listing as SEQ ID NO. 3 and SEQ ID NO.4. The Fluc is flanked by Nhe I (5') and EcoRI (3') sites. This was inserted into the vector pCDH-CMV-MCS-EF1-puro (from System Biosciences) and the resulting plasmid was called pCDH-puro-hFLuc, which is shown in FIG. 3.

Step 2: Cloning of Hygromycin Selection Marker into the Lentivector

The hygromycin resistance marker gene along with PGK promoter was synthesized with flanking enzyme sites Not I (5') and Sal I (3'). This cassette was digested and cloned into pCDH-CMV-EF1-puro (system Biosciences) replacing the EF1-puromycin region. The resulting construct was called pCDH-CMV-MCS-PGK-hygro which is shown in FIG. 4.

Step 3: Cloning of the Promoters—Human p21, Hamster GADD153 and p53 Response Elements The human p21 promoter was amplified from HEK 293 cells using the primers shown in sequence listing as SEQ ID No. 1 and SEQ ID No. 2. This promoter is flanked by Cla I (5') and Nhe I (3') sites. This was inserted into pCDH-puro-RLuc. This resulted in the removal of the CMV promoter from the lentivector. The plasmid was called pCDH-puro-p21-RLuc, which is shown in FIG. 5. The hamster GADD153 was synthesized and cloned into pCDH vector which is shown in FIG. 6. The GADD 153 promoter was flanked by Cla I (5') and Xba I-Nhe I (3') sites. This promoter was inserted into the pCDH-puro-hFLuc. This resulted in the removal of the CMV promoter from the lentivector. This plasmid was called pCDH-puro-GADD153-hFLuc, which is shown in FIG. 6. The p53 response element along with Polyoma UTR sequence was synthesized. This sequence was flanked by Cla I (5') and Xba I-Nhe I (3') sites. This construct was inserted into the pCDH-CMV-PGK-hygro-vector. This resulted in the removal of the CMV promoter from this lentivector. This plasmid was called pCDH-hygro-p53, which is shown in FIG. 7. The reporter gene beta galactosidase was synthesized with flanking enzyme sites Xba I-Nhe I (5') and Not I (3') and cloned into pCDH-Hygro-p53 to yield pCDH-hygro-p53-Bgal vector as shown in FIG. 8.

Primers used to amplify human p21 gene promoter from HEK 293 cell line is shown in sequence listing as SEQ ID No. 1 and SEQ ID No.2. The DNA sequences of each of the expression cassettes in the plasmids pCDH-puro-p21-RLuc, pCDH-puro-GADD153-hFLuc and pCDH-hygro-p53-Bgal are shown in the sequence listings as SEQ ID No. 5, 6 and 7, respectively.

Step 4: Engineering Stable Cell Line Expressing the Biosensor Reporter Cassettes The pPACK Plasmids (System Biosciences) were co-transfected into HEK 293T producer cells with the expression construct pCDH-puro-p21-RLuc that contained the genetic elements required for packaging, transduction, and expression, the cells (called 'packaging' or 'producer' cells) efficiently packaged the expression construct into highly transducible VSV-G-pseudotyped lentiviral particles. The lentiviral particles were concentrated by ultracentrifugation technique and were used to transduce HCT116 cell line, the human colon cancer cell line. The single cell clones bearing the Biosensor Reporter cassette were selected over two weeks under puromycin (2 μg/ml). The HCT116 cells transformed with pCDH-puro-p21-RLuc are referred to herein as HCT116-p21RLuc.

The pPACK Plasmids (System Biosciences) were co-transfected into HEK 293T producer cells with the expression construct pCDH-puro-GADD153-hFLuc that contained the genetic elements required for packaging, transduction, and expression, the cells (called 'packaging' or 'producer' cells) efficiently packaged the expression construct into highly transducible VSV-G-pseudotyped lentiviral particles. The lentiviral particles were concentrated by ultracentrifugation technique and were used to transduce HCT116-p21RLuc. The single cell clones bearing both the Biosensor Reporter cassettes, p21-RLuc and GADD153-hFLuc, were selected over two weeks under puromycin (2 µg/ml). The resulting stable cell line is referred to herein as HCT116-p21RLuc-GADD153hFLuc.

The pPACK Plasmids were co-transfected into HEK 293T producer cells with the expression construct pCDH-hygro-p53-Bgal that contained the genetic elements required for packaging, transduction, and expression, the cells (called 'packaging' or 'producer' cells) efficiently packaged the expression construct into highly transducible VSV-G-pseudotyped lentiviral particles. The lentiviral particles were concentrated by ultracentrifugation technique and were used to transduce HCT116-p21RLuc-GADD153hFLuc. The single cell clones bearing all three Biosensor Reporter cassettes, p21-RLuc, GADD153-hFLuc and p53-Bgal were selected over two weeks under hygromycin (0.2 mg/ml). The resulting stable cell line is referred to herein as HCT116-p21RLuc-GADD153hFLuc-p53Bgal.

The present invention describes a preferred assay for measuring genotoxicity of a test compound using cell line HCT116-p21RLuc-GADD153FLuc-p53bgal which has the promoters, p21, GADD 153 and p53. The assay is performed on a 96-well plate and using a microplate reader capable of luminescence readings.

EXAMPLE 2

Microplate Preparation

The assay is carried out in a 96-well, white, clear-bottomed microplates. For example F96 MicroWell™ Plates, Cat. No. 136101, from Nalgene Nunc, USA. The microplates are effectively filled using multi-channel pipette.

Assay Protocol

The assay protocol standardized by us is described here. A stock of the test compound is prepared in 2% v/v solvents (including but not limited to DMSO or PBS) and this stock is used to make serial dilutions for the assay. The maximum testing dose of the compounds is set at 1 mM or 500 µg/ml or less if limited by solubility or cytotoxicity. The test compound is assayed for cell viability by standard cell viability/cytotoxicity assays (for example MTT assay as shown in the graphs).

The MTT assay is performed using the MTT reagent (Sigma) dissolved in PBS (5 mg/ml). Briefly, the Genotox sensor cells are incubated with ten fold serial dilutions of the test compound in a 96-well microplate. After 24 h of incubation, 10 µl of the MTT solution is added to each well of the 96-well plate and incubated for 1 hour at 37° C. The medium is discarded (in a fume hood) and 100 µl DMSO is added to the wells. The plate is shaken for 10 min and absorbance is measured at 540 nm.

For the genotoxicity assay, 16 h prior to compound treatment, the engineered Anthem's Genotox sensor cells are seeded in 96-well microplates (10,000 cells per well). The following controls are included, untreated cells, 1% DMSO alone (to confirm the lack of dilutent absorbance), growth medium alone to confirm the lack of any contaminations, vehicle control (solvent control) and positive test control in serial dilutions. The test compound is added in two-fold serial dilutions and the microplate is incubated at 37 C, 5% CO2 and 95% humidity for 24 or 48 h depending on the experiment requirements.

The cells are lysed after 24 or 48 h with the 60 µl of lysis buffer per well (the lysis buffer composition has been optimized at Anthem Biosciences to be compatible with luciferase and beta galactosidase assays; 50 ml of Lysis buffer contains 7.5 ml of 1M HEPES at pH 8.0, 125 µl of Triton X 100, 50 mg of Porcine gelatin, 5 ml of glycerol and 25 µl of Antifoam). For each of the luciferase assays (Renilla and Firefly luciferase) 10 µl of the lysate is used, while 30 µl of the lysate is used for the beta galactosidase assay and total protein is estimated using the remaining 10 µl of the lysate by Bradford reagent.

The Renilla luciferase assay is performed using luciferase assay buffer (0.5 M NaCl, 0.1 M Potassium phosphate buffer pH 7.2, 1 mM Di-Sodium EDTA, 1 mg/mL porcine gelatin, 50 mM Potassium iodide) containing 1 µg/well coelentrazine (1 mg/ml stock prepared in 100% methanol). The firefly luciferase assay is performed with the same luciferase assay buffer containing 100 µM D luciferin, 150 µM ATP and 80 µM Coenzyme A. The assay plate is gently shaken for 10 minutes on a microplate shaker (to fully mix the contents of each well). Then the plate is taken to the microplate reader and the luminescence data are collected from the microplates. A microplate reader that has luminescence functionality is chosen (for example, Synergy HT multidetection microplate reader from BioTek). The Luminiscence data are collected with an integration time of 10 seconds and a delay of 2 seconds.

The beta galactosidase assay is carried out with Z assay buffer (50 ml buffer contains 0.4265 g of $Na_2HPO_4$, 0.275 g of $NaH_2PO_4$, 500 µl of 1M KCl, 50 µl of 1M $MgSO_4$; for every 10 ml, 27 µl of Beta mercaptoethanol is added) and the substrate o-nitrophenyl-β-D-galactosidase ONPG (1 ml of 10× ONPG stock-20 mg/ml). Once the yellow colour develops, 50 µl 1M Na2CO3 is added per well and the reading is taken at A420.

The luminescence and absorbance data are transported into Microsoft excel spreadsheet and the fold change in the reporter gene expressions is calculated by normalizing with the data from vehicle treated control wells. The graph is plotted with test compound concentrations on X axis, cell viability percentage (from MTT assay) on primary Y axis and reporter gene fold induction on the secondary Y axis. The cell viability threshold is set at 80% and the cytotoxicity LEC is defined as the lowest effective test concentration that reduced cell viability by 20% compared to untreated control. The genotoxic threshold is set at 1.5 fold change (i.e. 50% more than vehicle treated control). The genotoxic LEC is the lowest effective test concentration that produced at least one of the reporter gene inductions of more than 1.5 threshold. The genotoxicity threshold is not calculated for test concentrations that result in less than 50% cell viability.

The current invention also includes assay for detection of pro-mutagens or progenotoxins by treating the compounds with S9 fraction. S9 fraction is a liver extract (known to skilled person) which allows detection of metabolites generated from the compounds in the liver.

The genotoxic potential of metabolites of test compounds is assessed by incubating the compound in the Anthem's Genotox sensor cells for 3 hours with S9 of Aroclor 1254-treated rats (1% mix), procured from Moltox, Cat #11-101.5. The S9 fraction is used in combination with enzyme cofactors (example: 5 mM of Glucose-6-phosphate and 0.5 mM of β-nicotinamide adenine dinucleotide phosphate). The S9 mix is used at 1% v/v in the assay microplate. The cells are washed after 3 h with PBS to remove the S9 fraction and tested for genotoxicity after 24 hours. The assay conditions, assay time points, time of exposure to S9, source of S9 fraction can be modified according to the test compound and experiment.

The metabolic activation assay always includes a positive control (Cyclophosphamide, a known promutagen) and a solvent control. As mentioned previously, the genotoxic threshold is set at 1.5 fold induction of reporter gene (s) expression(s) over the solvent control (i.e. a 50% increase). The test compound is concluded as a positive genotoxin when the reporter gene (s) induction (s) is (are) over 1.5 fold. Table 1 shows sample of compounds screened using this assay wherein '+' positive for genotoxicity; '−' negative for genotoxicity; MA: metabolic activation using S9 fraction mix'.

Therefore the present invention features a method to express more than one DNA-damage inducible gene promoters that drive the expression of multiple reporter gene proteins. Diverse genotoxic signaling pathways can be detected by harnessing the potential of more than one type of promoter that are known to respond to genotoxic insult. Hence, the present invention describes a platform that can be adapted to serve as a high throughput screening aid.

EXAMPLE 3

Induction of the Biosensors Using Known Genotoxins

As an example of the reporter induction, HCT116-p21RLuc-GADD153hFLuc-p53Bgal cells treated with different concentrations of, Methyl methanesulphonate (a direct acting genotoxin) and cyclophosphamide (a progenotoxin) is shown in FIGS. 9, 10A and 10B. These two compounds are known to those skilled in the art as genotoxic agents and may be used as positive controls when using the method of the invention.

$10^3$ cells were seeded per well in 100 µl of McCoy's media with 10% FBS was incubated overnight (37° C., 5% CO2, 100% humidity) in a 96-well plates (as two sets). The next day, the cells were incubated with serial two fold dilutions of MMS and Cyclophosphamide dissolved in 1% v/v aqueous DMSO for 24 h. The cells treated with cyclophosphamide were incubated with S9 fraction mix as described above for 3 h and later washed with PBS. After incubation of 24 h, the cells were washed in PBS and MTT assay was performed on one set of plates to assess the cell viability. The cells in the other set of plates were lysed with the 100 µl of lysis buffer (50 ml of Lysis buffer contains 7.5 ml of 1M HEPES at pH 8.0, 125 µl of Triton X 100, 50 mg of Porcine gelatin, 5 ml of glycerol and 25 µl of Antifoam). 10 µl of the cell lysate was mixed with 100 µl of luciferase assay buffer (Luciferase assay buffer composition: 0.5 M NaCl, 0.1 M Potassium phosphate buffer pH 7.2, 1 mM Di-Sodium EDTA, 1 mg/mL porcine gelatin, 50 mM Potassium iodide) in a 96-well white microplate. To each well 1 µg of the RLuc substrate, coelenterazine (1 mg/ml coelenterazine stock solution is prepared in 100% methanol and stored in −80° C. freezer) was added. The plate was gently shaken for 10 minutes on a microplate shaker and then taken to the microplate reader to obtain the luminescence reading. 10 µl of the cell lysate was mixed with 100 µl of FLuc assay buffer in a 96-well white microplate. The firefly luciferase assay is performed with 10 µl of the cell lysate and 100 µl luciferase assay buffer containing 100 µM D luciferin, 150 µM ATP and 80 µM Coenzyme A. The beta galactosidase assay was carried out with 30 µl of lysate and Z assay buffer (50 ml buffer contains 0.4265 g of $Na_2HPO_4$, 0.275 g of $NaH_2PO_4$, 500 µl of 1M KCl, 50 µl of 1M $MgSO_4$; for every 10 ml, 27 µl of Beta mercaptoethanol is added) and the substrate o-nitrophenyl-β-D-galactosidase ONPG (1 ml of 10× ONPG stock-20 mg/ml). Once the yellow colour developed, 50 µl 1M Na2CO3 was added per well and the reading was taken at A420.

This was repeated three times and the average induction and standard errors were calculated. The results are illustrated in FIGS. 9 and 10A and 10B.

TABLE 1

| Compound | Class of the compound | Anthem's Genotox assay: Result (assay time in h), LEC in µg/ml, promoter(s) that was(were) induced |
|---|---|---|
| 2-Acetamidofluorene | Hepatic carcinogen | +(24 h), 6.977, GADD153 |
| 4,4-Oxydianiline | Polymer resins | +(24 h), 100.12, p21 and GADD153 |
| AraC arabinoside | Chemotherapeutic agent | +(24 h), 0.785, p21 |
| Cyclophosphamide | Chemotherapeutic agent | +(24 h, MA), >55.82, p21 |
| D-Mannitol | non genotoxic control | — |
| DMSO | solvent used in the assay | — |
| Etoposide | Topoisomerase inhibitor | +(24 h), 6.25, p21 |
| Methyl methanesulphonate | Direct acting genotoxin | +(24 h), 6.2, GADD153 and p53 |
| Ofloxacin | Anti bacterial | +(24 h), 750.0, p53 and p21 |
| Querceti3n | Flavinoid | +(24 h), 6.25, GADD153 |

Sequence Listing Free Text

The invention claimed is:

1. A eukaryotic cell comprising a first expression cassette which includes a DNA sequence encoding Renilla Luciferase (RLuc) and derivatives thereof as a reporter protein, operatively linked to human p21 gene promoter; a second expression cassette which includes a DNA sequence encoding humanized Firefly Luciferase (hFLuc) and derivatives thereof as a reporter protein, operatively linked to hamster GADD153 gene promoter; and a third expression cassette which includes a DNA sequence encoding beta galactosidase (Bgal) and derivatives thereof as reporter protein, operatively linked to p53 response element and polyoma virus UTR as promoter.

2. The cell as claimed in claim 1, wherein expression of the DNA sequence encoding reporter protein is activated in response to genome damage.

3. The cell as claimed in claim 1, wherein the human p21 gene promoter and/or the hamster GADD153 gene promoter and/or the p53 response element sequences induces RNA polymerase to bind to the DNA sequence and start transcribing the DNA sequence encoding the reporter proteins Rluc and/or FLuc and/or Bgal respectively.

4. The cell as claimed in claim 3, wherein the promoter sequence of human p21 is obtained from pCDH-puro-p21-RLuc plasmid.

5. The cell as claimed in claim 3, wherein the promoter sequence of hamster GADD153 is obtained from pCDH-puro-GADD153-hFLuc plasmid.

6. The cell as claimed in claim 3, wherein the promoter sequence of human p53 is obtained from pCDH-hygro-p53-Bgal plasmid.

7. The cell as claimed in claim 4, wherein nucleotide sequence encoding the human p21 gene promoter is shown at position 1961 to 4456 of SEQ ID NO: 5.

8. The cell as claimed in claim 5, wherein nucleotide sequence encoding the hamster GADD 153 gene promoter is shown at position 1961 to 2741 of SEQ ID NO: 6.

9. The cell as claimed in claim 6, wherein nucleotide sequence encoding the human p53 gene promoter is shown at position 1932 to 2380 of SEQ ID NO: 7.

10. The cell as claimed in claim 1, wherein the expression cassette is delivered to the cell ectopically by lentiviral system.

11. A high throughput screening method for detecting the presence of genotoxic agent causing DNA damage, said method comprising acts of:
    a) subjecting the cell as claimed in claim 1 to a genotoxic agent; and
    b) monitoring expression of light emitting reporter protein from the cell for detecting the presence of the genotoxic agent causing DNA damage.

* * * * *